US011332731B2

(12) United States Patent
Zhou et al.

(10) Patent No.: US 11,332,731 B2
(45) Date of Patent: May 17, 2022

(54) NITRILE HYDRATASE MUTANT, GENETICALLY ENGINEERED BACTERIUM CONTAINING MUTANT AND APPLICATIONS THEREOF

(71) Applicant: Jiangnan University, Wuxi (CN)

(72) Inventors: Zhemin Zhou, Wuxi (CN); Zhongmei Liu, Wuxi (CN); Junling Guo, Wuxi (CN); Li Zhou, Wuxi (CN); Wenjing Cui, Wuxi (CN); Yao Lan, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/208,027

(22) Filed: Mar. 22, 2021

(65) Prior Publication Data
US 2021/0207118 A1   Jul. 8, 2021

Related U.S. Application Data

(63) Continuation of application No. PCT/CN2019/071964, filed on Jan. 16, 2019.

(51) Int. Cl.
*C12N 9/88* (2006.01)
*C12N 15/52* (2006.01)
(Continued)

(52) U.S. Cl.
CPC ............. *C12N 9/88* (2013.01); *C12N 1/20* (2013.01); *C12N 15/52* (2013.01); *C12N 15/70* (2013.01);
(Continued)

(58) Field of Classification Search
None
See application file for complete search history.

(56) References Cited

U.S. PATENT DOCUMENTS

| 5,728,556 A | 3/1998 | Dicosimo et al. |
| 2011/0212506 A1* | 9/2011 | Matsumoto ............. C12N 9/88 435/232 |

(Continued)

FOREIGN PATENT DOCUMENTS

| CN | 1584024 A | 2/2005 |
| CN | 102216455 A | 10/2011 |

(Continued)

*Primary Examiner* — Richard C Ekstrom
(74) *Attorney, Agent, or Firm* — IPro, PLLC

(57) ABSTRACT

The disclosure discloses a nitrile hydratase mutant, a genetically engineered bacterium containing the mutant and applications thereof, and belongs to the technical field of enzyme engineering. In the disclosure, glycine at position 47 of a nitrile hydratase mutant αL6T/A19V/F126Y-βM46K/E108R/S212Y (disclosed in the patent of disclosure CN102216455A) is mutated to asparagine. The obtained new mutant enzyme has better temperature tolerance and tolerance to a product, and is conducive to future industrial production. The recombinant strain containing the nitrile hydratase mutant is fermented at high density, and 3-cyanopyridine is used as a substrate to carry out a whole-cell catalytic reaction to prepare nicotinamide. Compared with a chemical production method, the method has a safe and clean production process and no environmental pollution. Compared with an enzymatic method, the substrate price is cheap and the catalytic efficiency is high. The yield of the final product nicotinamide is over 95%, the concentration reaches 680 g/L, and the separation and purification steps of the product are simplified.

14 Claims, 4 Drawing Sheets

Specification includes a Sequence Listing.

(51) Int. Cl.
  *C12N 15/70* (2006.01)
  *C12N 1/20* (2006.01)
  *C12P 13/02* (2006.01)

(52) U.S. Cl.
  CPC ....... *C12P 13/02* (2013.01); *C12Y 402/01084* (2013.01)

(56) References Cited

U.S. PATENT DOCUMENTS

2019/0367897 A1* 12/2019 Tateno .................. C12N 9/88
2021/0207118 A1*  7/2021 Zhou .................... C12N 9/88

FOREIGN PATENT DOCUMENTS

| CN | 102492697 A | 6/2012 |
| CN | 102899345 A | 1/2013 |
| CN | 106544336 A | 3/2017 |

\* cited by examiner

SEQUENCE LISTING

```
<160> NUMBER OF SEQ ID NOS: 10

<210> SEQ ID NO 1
<211> LENGTH: 205
<212> TYPE: PRT
<213> ORGANISM: Artificial sequence
<220> FEATURE:
<223> OTHER INFORMATION: Protein translated from synthetic DNA

<400> SEQUENCE: 1

Met Thr Glu Asn Ile Thr Arg Lys Ser Asp Glu Glu Ile Gln Lys Glu
1               5                   10                  15

Ile Thr Val Arg Val Lys Ala Leu Glu Ser Met Leu Ile Glu Gln Gly
                20                  25                  30

Ile Leu Thr Thr Ser Met Ile Asp Arg Met Ala Glu Ile Tyr Glu Asn
            35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Cys Thr Leu Cys Ser
                100                 105                 110

Cys Tyr Pro Trp Pro Val Leu Gly Leu Pro Pro Asn Trp Tyr Lys Glu
            115                 120                 125

Pro Gln Tyr Arg Ser Arg Val Val Arg Glu Pro Arg Gln Leu Leu Lys
    130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 2
<211> LENGTH: 241
<212> TYPE: PRT
<213> ORGANISM: Artificial sequence
<220> FEATURE:
<223> OTHER INFORMATION: Protein translated from synthetic DNA

<400> SEQUENCE: 2

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30
```

```
Ala Phe Ala Met Phe Pro Ala Thr Phe Arg Ala Gly Phe Lys Asn Leu
        35                  40                  45

Asp Glu Phe Arg Phe Gly Ile Glu Gln Met Asn Pro Ala Glu Tyr Leu
 50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Leu Glu Arg Arg Thr Gln
                85                  90                  95

Tyr Tyr Arg Glu Asn Pro Asp Ala Pro Leu Pro Arg His Glu Gln Lys
                100                 105                 110

Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Ala Gln Glu Leu Trp Gly Pro Glu Gly
                195                 200                 205

Asp Pro Asn Tyr Ser Val Tyr Tyr Asp Cys Trp Glu Pro Tyr Ile Glu
    210                 215                 220

Leu Val Asp Thr Lys Ala Ala Ala Ala Trp Ser His Pro Gln Phe Glu
225                 230                 235                 240

Lys

<210> SEQ ID NO 3
<211> LENGTH: 144
<212> TYPE: PRT
<213> ORGANISM: Pseudonocardia thermophila

<400> SEQUENCE: 3

Met Ser Ala Glu Ala Lys Val Arg Leu Lys His Cys Pro Thr Ala Glu
1               5                   10                  15

Asp Arg Ala Ala Asp Ala Leu Leu Ala Gln Leu Pro Gly Gly Asp
                20                  25                  30

Arg Ala Leu Asp Arg Gly Phe Asp Glu Pro Trp Gln Leu Arg Ala Phe
            35                  40                  45

Ala Leu Ala Val Ala Ala Cys Arg Ala Gly Arg Phe Glu Trp Lys Gln
50                  55                  60

Leu Gln Gln Ala Leu Ile Ser Ser Ile Gly Glu Trp Glu Arg Thr His
65                  70                  75                  80

Asp Leu Asp Asp Pro Ser Trp Ser Tyr Tyr Glu His Phe Val Ala Ala
                85                  90                  95

Leu Glu Ser Val Leu Gly Glu Glu Gly Ile Val Glu Pro Glu Ala Leu
                100                 105                 110

Asp Glu Arg Thr Ala Glu Val Leu Ala Asn Pro Asn Lys Asp His
            115                 120                 125

His Gly Pro His Leu Glu Pro Val Ala Val His Pro Ala Val Arg Ser
130                 135                 140

<210> SEQ ID NO 4
```

```
<211> LENGTH: 205
<212> TYPE: PRT
<213> ORGANISM: Pseudonocardia thermophila

<400> SEQUENCE: 4

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
        115                 120                 125

Pro Gln Tyr Arg Ser Arg Val Val Arg Glu Pro Arg Gln Leu Leu Lys
    130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 5
<211> LENGTH: 241
<212> TYPE: PRT
<213> ORGANISM: Pseudonocardia thermophila

<400> SEQUENCE: 5

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140
```

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala Ala Trp Ser His Pro Gln Phe Glu
225                 230                 235                 240

Lys

<210> SEQ ID NO 6
<211> LENGTH: 31
<212> TYPE: DNA
<213> ORGANISM: Artificial sequence
<220> FEATURE:
<223> OTHER INFORMATION: synthetic DNA

<400> SEQUENCE: 6
ctgttgaata taagaataag gaggtatttt a                                31

<210> SEQ ID NO 7
<211> LENGTH: 21
<212> TYPE: DNA
<213> ORGANISM: Artificial sequence
<220> FEATURE:
<223> OTHER INFORMATION: synthetic DNA

<400> SEQUENCE: 7
tgaatattaa ggaggttatt t                                          21

<210> SEQ ID NO 8
<211> LENGTH: 1831
<212> TYPE: DNA
<213> ORGANISM: Artificial sequence
<220> FEATURE:
<223> OTHER INFORMATION: synthetic DNA

<400> SEQUENCE: 8
atgaatggcg tttatgatgt tggtggcacc gatggtctgg gtccgattaa tcgcccggcc    60
gatgaaccgg tttttcgcgc cgaatgggaa aaagttgcat tgccatgtt tccggcaacc    120 tttcgcgcag gttttaaaaa tctggatgaa tttcgttttg gcattgaaca gatgaatccg    180
gcagaatatc tggaaagtcc gtattattgg cattggattc gtacctatat tcatcatggc    240
gtgcgtaccg gtaaaattga tctggaagaa ctggaacgtc gtacccagta ttatcgtgaa    300
aatccggatg ccccgctgcc gcgccatgaa cagaaaccgg aactgattga atttgtgaat    360
caggccgttt atggcggcct gccggcaagc cgtgaagttg atcgtccgcc gaaattcaaa    420
gaaggtgacg tggtgcgctt tagcaccgcc agtccgaaag ccatgcacg tcgtgcccgc    480 tatgtgcgtg gcaaaaccgg taccgtggtt aaacatcatg gtgcatatat ctatccggat    540
accgccggta atggcctggg tgaatgtccg aacatctgt ataccgttcg ctttaccgca    600
caggaactgt ggggcccgga aggtgacccg aattatagtg tttattatga ttgctgggag    660
ccgtatattg aactggtgga taccaaagca gcagccgcat ggagccaccc gcagttcgaa    720

```
aagtgactgt tgaatataag aataaggagg tattttaatg accgaaaaca tcacccgtaa    780
aagcgatgaa gaaattcaga agaaatcac cgtgcgcgtt aaagccctgg aaagtatgct    840
gattgaacag ggcattctga ccaccagtat gattgatcgt atggccgaaa tctatgaaaa    900
tgaagttggc ccgcatctgg gcgccaaagt ggtggttaaa gcctggaccg atccggagtt    960
taaaaaacgc ctgctggccg atggcaccga agcatgtaaa gaactgggca ttggtggcct   1020
gcagggcgaa gatatgatgt gggtggaaaa taccgatgaa gtgcatcatg tggtggtttg   1080
taccctgtgc agttgctatc cgtggccggt tctgggcctg ccgccgaatt ggtataaaga   1140
accgcagtat cgcagccgtg ttgtgcgtga accgcgtcag ctgctgaaag aagaatttgg   1200
ttttgaagtt ccgccgagta aagaaattaa ggtttgggat agcagcagcg aaatgcgttt   1260
tgtggtgctg ccgcagcgtc cggccggtac agatggttgg agcgaagaag aactggccac   1320
cctggtgacc cgcgaaagta tgattggtgt tgaaccggcc aaagcagtgg catgatgaat   1380
attaaggagg ttatttatga gcgctgaagc caaagtgcgt ctgaaacatt gtccgaccgc   1440
cgaagatcgc gccgccgcag atgcactgct ggcacagctg ccgggcggcg accgcgcgct   1500
cgatcgcggt tttgatgaac cgtggcagct gcgcgccttt gccctggccg tggccgcctg   1560
tcgcgccggc cgctttgaat ggaaacagct gcagcaggcc ctgattagca gtattggcga   1620
atgggaacgt acccatgatc tggatgatcc gagctggagc tattatgaac attttgtggc   1680
cgcactggaa agtgtgctgg gcgaagaagg tattgttgaa ccggaagcac tggatgaacg   1740
caccgccgaa gttctggcca atccgccgaa taaggatcat catggcccgc atctggaacc   1800
ggttgcagtg catccggcag ttcgcagcta a                                 1831
```

<210> SEQ ID NO 9
<211> LENGTH: 33
<212> TYPE: DNA
<213> ORGANISM: Artificial sequence
<220> FEATURE:
<223> OTHER INFORMATION: synthetic DNA

<400> SEQUENCE: 9

```
cgcgcaggtt ttaaaaatct ggatgaattt cgt                                 33
```

<210> SEQ ID NO 10
<211> LENGTH: 35
<212> TYPE: DNA
<213> ORGANISM: Artificial sequence
<220> FEATURE:
<223> OTHER INFORMATION: synthetic DNA

<400> SEQUENCE: 10

```
ttcatccaga tttttaaaac ctgcgcgaaa ggttg                               35
```

NITRILE HYDRATASE MUTANT, GENETICALLY ENGINEERED BACTERIUM CONTAINING MUTANT AND APPLICATIONS THEREOF

TECHNICAL FIELD

The disclosure relates to a nitrile hydratase mutant, a genetically engineered bacterium containing the mutant and applications thereof, and belongs to the technical field of enzyme engineering.

BACKGROUND

Nitrile hydratase (NHase) can be used for catalysis of 3-cyanopyridine to nicotinamide with higher medicinal value. Nicotinamide is a vitamin and has been widely used in feed, food, pharmacy and other industries. Nicotinamide is in great demand in the market, and it is estimated that more than 2,000 tons of nicotinamide is needed per year. However, the current production level of nicotinamide in China is not high and the scale is small, and a large amount of imports, about 1,000 tons of nicotinamide is needed. Therefore, use of NHase in the production of nicotinamide has great potential. However, the reaction is an exothermic process, so high temperature in the production process will affect the performance of enzyme activity. The main reason is that the high temperature affects the structure of the enzyme, leading to a decrease in enzyme activity, which in turn leads to a large amount of energy consumption and increases production costs. At the same time, both the substrates and products of the nitrile hydratase are organic matter, and high-concentration organic matter have a great destructive effect on the structure of the enzyme, causing the enzyme activity to decrease rapidly and the catalytic activity to decrease. Therefore, it is particularly important to improve the thermal stability and tolerance of the nitrile hydratase to substrates and products in a catalysis process of production.

At present, *Rhodococcus rhodochrous* J1 is mainly used in industrial production for catalysis to produce nicotinamide by adopting a method of substrate feeding in batches. However, the growth cycle of *Rhodococcus* is long, requiring 100 h, and the production efficiency is not high, only 162 g/(L·h). There are also reports of the production of nicotinamide by recombinant bacteria, but the final product concentration is low, only 240 g/L.

Currently, the nitrile hydratase is widespread in nature, and the most reported nitrile hydratase is from bacteria and actinomycetes, such as the nitrile hydratase from *Rhodococcus, Nocardia, Bacillus*, and *Pseudonocardia*. At present, most of the nitrile hydratase is not high in thermal stability. Therefore, choosing nitrile hydratase derived from *Pseudonocardia thermophila* with improved stability has important application value for the industrial production of amide products.

SUMMARY

A first objective of the disclosure is to provide a nitrile hydratase mutant containing a PtNHase-α subunit, a PtNHase-β subunit and a regulatory protein PtNHase-p. The amino acid sequence of the PtNHase-α subunit is set forth in SEQ ID NO:1, the amino acid sequence of the PtNHase-β subunit is set forth in SEQ ID NO:2, and the amino acid sequence of the regulatory protein PtNHase-p is set forth in SEQ ID NO:3.

In one implementation, the mutant takes the nitrile hydratase, the amino acid sequences of an α subunit, a β subunit, and a regulatory protein of which are set forth in SEQ ID NO:4, SEQ ID NO:5, and SEQ ID NO:3 respectively, as a parent enzyme. In the α subunit, leucine at position 6 is mutated to threonine, alanine at position 19 is mutated to valine, and phenylalanine at position 126 is mutated to tyrosine. In the β subunit, methionine at position 46 is mutated to lysine, glycine at position 47 is mutated to asparagine, glutamic acid at position 108 is mutated to arginine, and serine at position 212 is mutated to tyrosine.

A second objective of the disclosure is to provide a gene encoding the nitrile hydratase mutant.

In one implementation, the nucleotide sequence of the gene is set forth in SEQ ID NO:8.

A third objective of the disclosure is to provide a cell expressing the above nitrile hydratase mutant.

In one implementation of the disclosure, an *E. coli* BL21 cell is included.

In one implementation of the disclosure, pET 24a(+) is used as an expression vector.

In one implementation of the disclosure, a method for constructing the above cell is: the gene encoding the nitrile hydratase mutant is ligated with an expression vector, and transformed into *E. coli*.

In one implementation of the disclosure, the gene encoding the nitrile hydratase mutant set forth in SEQ ID NO:8 is ligated with an expression vector, and transformed into *E. coli*.

In one implementation of the disclosure, the gene encoding the nitrile hydratase mutant as set forth in SEQ ID NO:8 is formed by sequentially ligating the gene encoding the PtNHase-β subunit as set forth in SEQ ID NO:2, a gene encoding a spacer sequence a as set forth in SEQ ID NO:6, the gene encoding the PtNHase-α subunit as set forth in SEQ ID NO:1, a gene encoding a spacer sequence b as set forth in SEQ ID NO:7, and the gene encoding the regulatory protein PtNHase-p as set forth in SEQ ID NO:3.

A fourth objective of the disclosure is to provide a composition containing the nitrile hydratase mutant.

In one implementation of the disclosure, a protective agent is included, but is not limited thereto.

A fifth objective of the disclosure is to provide applications of the nitrile hydratase mutant or the above cell in the production of products containing nicotinamide or acrylamide.

A sixth objective of the disclosure is to provide a method for producing nicotinamide or acrylamide. The nitrile hydratase mutant, or the above cell, or the above composition is used as a catalyst, and a transformation reaction is carried out with 3-cyanopyridine or acrylonitrile as a substrate.

In one implementation of the disclosure, 3-cyanopyridine or acrylonitrile is used as the substrate, fermentation is carried out using the cell, and a fermentation broth is used for whole-cell transformation to produce nicotinamide or acrylamide.

In one implementation of the disclosure, conditions for the cell fermentation are: a fermenter culture medium is inoculated with a recombinant *E. coli* broth cultured for 6-8 h at an inoculum concentration of 5-8%, and culture is performed at 35-38° C.; when the $OD_{600}$ reaches 70-75, the temperature is reduced to 28-30° C., and an inducer is added at a constant flow rate of 0.20-0.22 g/(L·h) to induce the culture for 35-40 h to end the fermentation.

In one implementation of the disclosure, whole-cell transformation reaction conditions are: the temperature is adjusted to 25-28° C., a mass ratio of the substrate 3-cyanopyridine to wet bacterial cells is 0.5-2, and the next batch of substrates is added after the substrate reacts completely.

In one implementation of the disclosure, whole-cell transformation reaction conditions are: the temperature is adjusted to 25-28° C., a mass ratio of the substrate acrylonitrile to wet bacterial cells is 1-1.5, and the next batch of substrates is added after the substrate reacts completely.

Beneficial Effects of the Disclosure:

First, the optimal temperature of the nitrile hydratase mutant αL6T/A19V/F126Y-βM46K/G47N/E108R/S212Y provided by the disclosure is 36° C., and the nitrile hydratase mutant still has 53% residual enzyme activity after being treated at 50° C. for 80 minutes. Compared with the control enzyme mutant αL6T/A19V/F126Y-βM46K/E108R/S212Y (in the a subunit of the parent enzyme, leucine at position 6 is mutated to threonine, alanine at position 19 is mutated to valine, and phenylalanine at position 126 is mutated to tyrosine; in the β subunit, methionine at position 46 is mutated to lysine, glycine at position 47 is mutated to asparagine, glutamic acid at position 108 is mutated to arginine, and serine at position 212 is mutated to tyrosine) which has 37% residual enzyme activity after being treated at 50° C. for 80 minutes, the residual enzyme activity is increased by 43%, and the thermal stability of the mutant is significantly improved. When the concentration of the substrate 3-cyanopyridine is 0.2 M, the enzyme activity is the highest, which is defined as 100%, and the tolerance of the mutant enzyme to the substrate is not affected. After the mutant is treated with a product nicotinamide of 2 M for 20 min, the residual enzyme activity of the mutant enzyme increases from 28% of the control to 52%, so that the mutant also has better tolerance to the product. Therefore, the nitrile hydratase mutant αL6T/A19V/F126Y-βM46K/G47N/E108R/S212Y provided by the disclosure has good enzymatic properties and is beneficial to future industrial production.

Second, the disclosure constructs recombinant *E. coli* expressing the nitrile hydratase mutant αL6T/A19V/F126Y-βM46K/G47N/E108R/S212Y to obtain a nitrile hydratase strain with high enzyme activity, and the specific enzyme activity of the pure enzyme of the recombinant nitrile hydratase is 907.69 U/mg. The recombinant strain is subjected to high-density fermentation. 3-cyanopyridine and acrylonitrile are used as substrates, and a whole-cell catalytic reaction is carried out to prepare nicotinamide and acrylamide. The yield of nicotinamide reaches 680 g/L, and the yield of acrylamide reaches 514.8 g/L. Compared with the production of nicotinamide with *Rhodococcus rhodochrousil* for catalysis, the method has a yield of over 95% of the final products nicotinamide and acrylamide, simplifies the separation and purification steps of the products, and has short fermentation cycle and high production efficiency.

Figure 1:
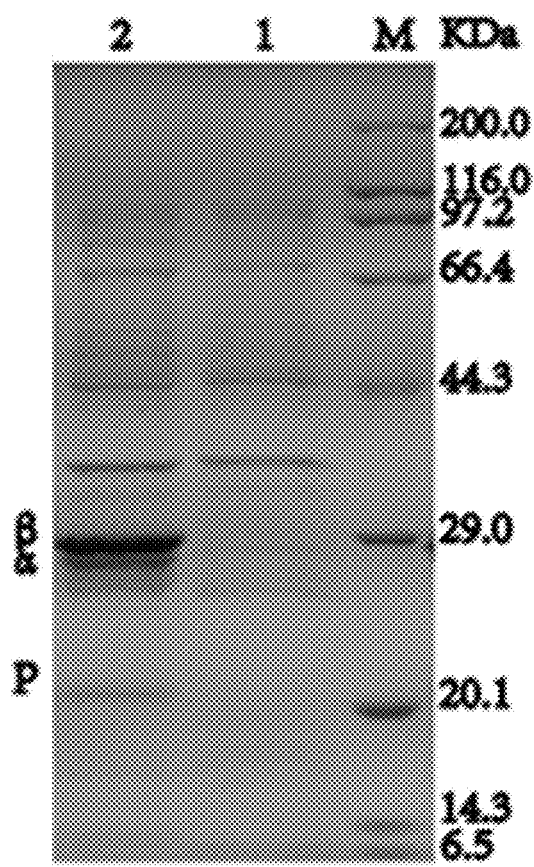
FIG. 1 is an SDS-PAGE electrophoretogram of PtNHase protein expression, wherein M is the protein molecular weight standard (6.5-200 KDa); 1 is the cell disruption supernatant of the *E. coli* BL21/pET24a-αL6T/A19V/F126Y-βM46K/E108R/S212Y control bacterium; and 2 is the cell disruption supernatant induced by the *E. coli* BL21/pET24a-αL6T/A19V/F126Y-βM46K/G47N/E108R/S212Y recombinant bacterium.

DETAILED DESCRIPTION (I) Definition of Enzyme Activity, Specific Enzyme Activity and Relative Enzyme Activity, and Method for Determining Enzyme Activity Definition of enzyme activity (U): The amount of enzyme required to convert 3-cyanopyridine to 1 μmol/L nicotinamide per minute is defined as 1 U.

Specific enzyme activity (U/mg): The enzyme activity per milligram of NHase.

Definition of relative enzyme activity: The enzyme activity of the mutant enzyme αL6T/A19V/F126Y-βM46K/G47N/E108R/S212Y reacting at pH of 8.4 and temperature of 36° C. for 10 minutes is defined as 100%.

Method for determining the enzyme activity of a fermentation broth: 100 μL of bacterial cells (dissolved in a phosphate buffer) with an $OD_{600}$ of 1.0 is added to 400 μL of a 125 mmol/L 3-cyanopyridine solution, the reaction is carried out at 25° C. for 10 min, and the reaction is stopped with 500 μL of acetonitrile. Immediately after adding the stop solution, the reaction solution is centrifuged at 4° C. and 12000 r/min for 1 min, and then the supernatant is pipetted. The reaction solution is filtered through a 0.22 μm microporous filter membrane and loaded on a C18 chromatographic column for HPLC analysis. The mobile phase is a mixed solution of acetonitrile and water (acetonitrile:water=1:2). The determination method of 3-cyanopyridine and nicotinamide is: the mobile phase is the mixed solution of acetonitrile and water (acetonitrile:water=1:2), the flow rate is 0.6 mL/min, the absorbance value is 215 nm, and the collection time is 12 min. Cell density: $OD_{600}$ is measured with a UV-1800PC ultraviolet-visible spectrophotometer, and conversion is carried out according to the relation between the absorbance value and OD. The conversion relation is: 1 g/L=0.3683 $OD_{600}$.

Method for determining the enzyme activity of the nitrile hydratase: The substrate is 490 μL of 200 mM 3-cyanopyridine. 10 μL of a pure enzyme solution with a concentration of 0.5 μg/μL or 10 μL of a broth with an OD of 10 is added, and the reaction is carried out at 36° C. for 10 min. The reaction is stopped with 500 μL of acetonitrile, and the reaction solution is centrifuged to remove precipitate. The supernatant is taken, filtered through a 0.22 μm membrane, and used as a sample for liquid phase determination.

(II) Culture Medium

LB culture medium: peptone 10 g/L, yeast extract 5 g/L, and NaCl 10 g/L.

Fermenter culture medium (g/L): glucose 12.0, potassium dihydrogen phosphate 13.5, diammonium hydrogen phosphate 4.0, citric acid 1.7, magnesium sulfate 1.68, and trace elements 10 mL.

Feed culture medium (g/L): glucose 500.0, magnesium sulfate 7.33, yeast extract 4.0, and tryptone 4.0.

Inducer (g/100 mL): lactose 10.0, and $CoCl_2 \cdot 6H_2O$ 0.8.

Trace elements (g/100 mL): ferrous sulfate heptahydrate 1.0, zinc sulfate heptahydrate 0.525, copper sulfate pentahydrate 0.3, manganese sulfate tetrahydrate 0.05, borax 0.023, calcium chloride 0.2, and ammonium molybdate 0.01.

(III) Method for Detecting Content of Nitrile Hydratase, Nicotinamide and Acrylamide by HPLC Reaction system of nitrile hydratase: The substrate is 490 μL of 200 mM 3-cyanopyridine. 10 μL of a pure enzyme solution with a concentration of 0.5 μg/μL or 10 μL of a broth with an OD of 10 under a wavelength of 600 nm is added, and the reaction is carried out at 36° C. for 10 min. Then the reaction is stopped with 500 μL of acetonitrile, and the reaction solution is centrifuged to remove precipitate. The supernatant is taken, filtered through a 0.22 μm membrane, and used as a sample for liquid phase determination.

Detection of the content of nitrile hydratase by HPLC: Agilent 1260 is used for HPLC detection. The mobile phase is a water acetonitrile buffer. The detection wavelength is 210 nm, the flow rate is 0.6 mL/min, and the chromatographic column is a C18 column.

Detection of the content of nicotinamide or acrylamide by HPLC: Agilent 1260 is used for HPLC detection. The mobile phase is a water acetonitrile buffer. The detection wavelength is 210 nm, the flow rate is 0.6 mL/min, and the chromatographic column is a C18 column.

(IV) Determination of Temperature Stability

The enzyme mutant αL6T/A19V/F126Y-βM46K/E108R/S212Y (the amino acid sequence of an α subunit is set forth in SEQ ID NO:11, and the amino acid sequence of a β subunit is set forth in SEQ ID NO:12) is used as a control.

The control and mutants are incubated in a KPB buffer with a pH of 8.4 at 50° C. for 20 minutes, 40 minutes, 60 minutes, 80 minutes, and 100 minutes respectively, and then the residual enzyme activity is measured to obtain temperature stability results.

(V) Determination of Tolerance to Substrate

The control and mutants are diluted in a KPB buffer with a pH of 8.4 to become broths with an OD of 10 at a wavelength of 600 nm. The residual enzyme activity is determined after incubation in 3-cyanopyridine at the concentrations of 200 mM, 400 mM, 600 mM, 800 mM, and 1000 mM respectively at 36° C. for 20 minutes, and the results of tolerance to the substrate are obtained.

(VI) Determination of Tolerance to Product

The control and mutants are diluted in KPB buffers with a pH of 8.4 to become broths with an OD of 10 at a wavelength of 600 nm. The residual enzyme activity is determined after incubation in nicotinamide at the concentrations of 0.5 M, 1 M, 1.5 M, and 2 M respectively at 36° C. for 20 minutes, and the results of tolerance to products are obtained.

Example 1 Construction of Recombinant E. coli (1) Construction of mutant αL6T/A19V/F126Y-βM46K/G47N/E108R/S212Y:

The nitrile hydratase mutant αL6T/A19V/F126Y-βM46K/E108R/S212Y gene was synthesized by chemical synthesis (the nucleotide sequence of an α subunit is set forth in SEQ ID NO: 13, and the nucleotide sequence of a β subunit is set forth in SEQ ID NO:14). The gene was cloned at the NdeI and Bpu10I restriction sites of a pET24a plasmid, and the process was completed by General Biosystems (Anhui) Co., Ltd. to obtain a pET24a-αL6T/A19V/F126Y-βM46K/E108R/S212Y recombinant plasmid. Using pET24a-αL6T/A19V/F126Y-βM46K/E108R/S212Y as a template, PCR was carried out under the conditions shown in Table 1. The sequence information of a forward primer used is set forth in SEQ ID NO:9, and the sequence information of a reverse primer used is set forth in SEQ ID NO:10. The PCR product was transformed into E. coli JM109 to obtain a recombinant plasmid pET24a-αL6T/A19V/F126Y-βM46K/G47N/E108R/S212Y carrying the gene encoding the mutant. The recombinant plasmid pET24a-αL6T/A19V/F126Y-βM46K/G47N/E108R/S212Y was transformed into an E. coli BL21 strain to obtain a recombinant strain BL21/pET24a-αL6T/A19V/F126Y-βM46K/G47N/E108R/S212Y.

A control plasmid and a control strain expressing the nitrile hydratase mutant αL6T/A19V/F126Y-βM46K/E108R/S212Y were constructed by a similar method.

TABLE 1

| Whole plasmid PCR amplification reaction system | |
|---|---|
| Regent | Amount |
| ddH$_2$O | 32 μL |
| 5× PS Buffer(Mg$^{2+}$ plus) | 10 μL |
| dNTP Mixture(2 mmol/L) | 4 μL |
| P1(10 mmol/L) | 1 μL |
| P2(10 mmol/L) | 1 μL |
| pET24a-αL6T/A19V/F126Y-βM46K/E108R/S212Y | 1 μL |
| Primer STAR HS DNA polymerase | 1 μL |
| Total | 50 μL |

PCR amplification reaction conditions:

| | | |
|---|---|---|
| 95° C. Initial denaturation | 5 min | |
| 95° C. Denaturation | 1 min | |
| 58° C. Annealing | 30 s | 30 cycles |
| 72° C. Extension | 2 min | |
| 72° C. Extension | 10 min | |

The PCR product was identified by an agarose gel electrophoresis method. Then the PCR product was purified, digested and transformed into E. coli BL21 competent cells.

(2) 4 mL of LB culture medium (peptone 10 g/L, yeast extract 5 g/L, and NaCl 10 g/L) containing kanamycin with a concentration of 100 μg/mL was inoculated with the BL21/pET24a-αL6T/A19V/F126Y-βM46K/G47N/E108R/S212Y recombinant E. coli, and culture was performed overnight with shaking at 37° C. and 200 r/min.

100 mL of LB expression culture medium (peptone 10 g/L, yeast extract 5 g/L, and NaCl 10 g/L) containing kanamycin with a concentration of 100 μg/mL was inoculated with the above overnight culture at an inoculum concentration of 1% (v/v). After shaking culture at 37° C.

and 200 r/min until the OD$_{600}$ reaches 0.6-0.8 at a wavelength of 600 nm, an inducer IPTG was added to 0.1 mM, the culture was induced at 20° C. for 12-18 h to obtain bacterial cells, and the bacterial cells were collected by centrifugation at 5000 g rotation speed.

(3) The recombinant bacterial cells were dissolved in 20 mL of binding buffer solution (20 mmol/L Na$_2$HPO$_4$, 280 mmol/L NaCl, and 6 mmol/L KCl). The reaction solution was sonicated and centrifuged at 13000 g for 25 min, and the supernatant was filtered by a 0.22 μm filter. A 1 mL strep Trap HP column was equilibrated with the binding buffer solution 10 times the column volume. Non-specifically adsorbed proteins were washed out with the binding buffer solution 15 times the column volume. The protein was eluted with 20 mM Na$_2$HPO$_4$, 280 mM NaCl, 6 mM KCl, and 2.5 mM dethiobiotin buffer 8 times the column volume. The sample was collected and analyzed by SDS-PAGE.

Example 2 Expression of Nitrile Hydratase 5 mL of LB culture medium containing kanamycin with a concentration of 100 μg/mL was inoculated with BL21/pET24a-αL6T/A19V/F126Y-βM46K/G47N/E108R/S212Y recombinant *E. coli*, and culture was performed overnight with shaking at 37° C. and 200 r/min. An LB culture medium containing kanamycin with a concentration of 100 μg/mL was inoculated with the above overnight culture at an inoculum concentration of 1%, and culture was performed at 37° C. and 200 r/min with shaking until the OD$_{600}$ of the broth was 0.6-0.8. IPTG was added to a final concentration of 0.4 mmol/L, and culture was induced at 20° C. for 16-20 h. Bacterial cells were collected and sonicated. The expression level of the nitrile hydratase recombinant protein was analyzed and identified by Tris-tricine SDS-PAGE. The results are shown in FIG. 1. After sonication and centrifugation at 12000 rpm for 60 min, the protein was purified with an affinity column Strep Trap FF, and the specific enzyme activity of pure enzyme of the recombinant nitrile hydratase was 907.69 U/mg.

Example 3 Determination of Thermal Stability

10 μL of the 0.5 mg/ml mutant enzyme purified in Example 1 was added to a 500 μL buffer reaction system (20 mmol/L Na$_2$HPO$_4$, 280 mmol/L NaCl, and 6 mmol/L KCl), and the reaction system was stored in a metal bath at 50° C. Samples were taken every 20 minutes to determine the residual enzyme activity.

Figure 2:
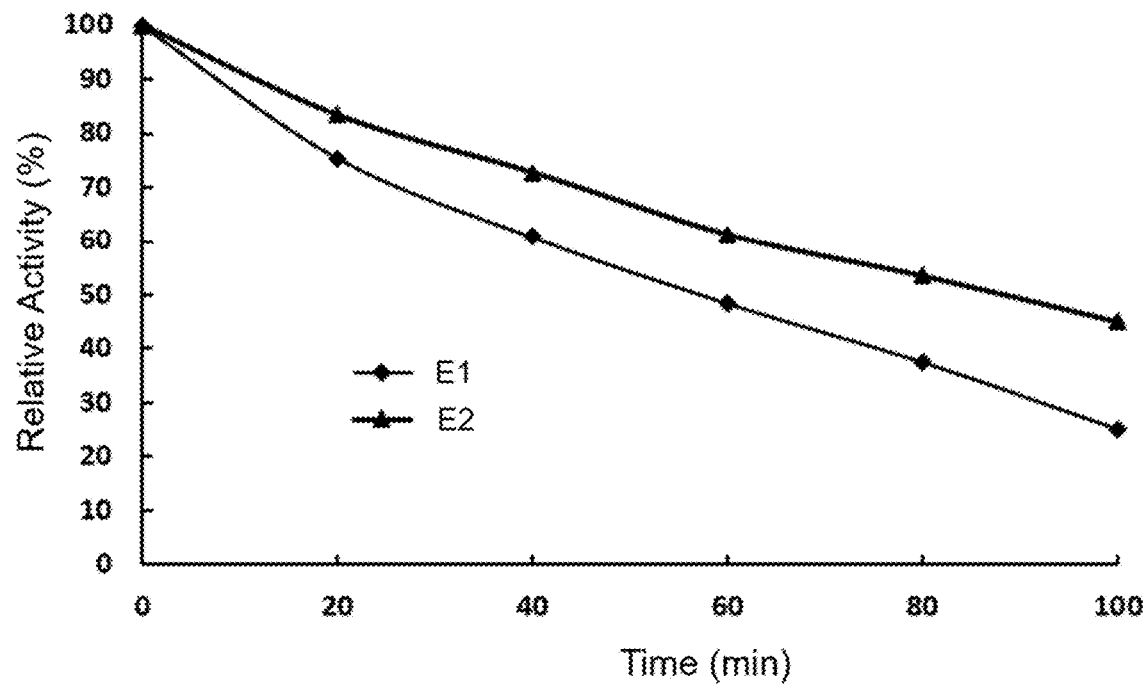
FIG. 2 shows a thermal stability curve of enzymes after storage at 50° C., wherein enzyme 1: αL6T/A19V/F126Y-βM46K/E108R/S212Y; and enzyme 2: αL6T/A19V/F126Y-βM46K/G47N/E108R/S212Y.

As shown in FIG. 2, it was found that after the mutant was treated at 50° C. for 80 min, the residual enzyme activity of the mutant enzyme increased from 37% of the control (the residual enzyme activity was 333 U/mg) to 53% (the residual enzyme activity was 424 U/mg); after treatment at 50° C. for 100 min, the relative enzyme activity of the mutant enzyme increased from 24% of the control (the residual enzyme activity was 216 U/mg) to 45% (the residual enzyme activity was 360 U/mg). The thermal stability of the mutant was significantly improved.

Example 4 Determination of Tolerance to Substrate

Solutions of the substrate with different concentrations of 0.2 M, 0.4 M, 0.6 M, 0.8 M, and 1 M were prepared. The control and mutant broths with an OD of 10 at a wavelength of 600 nm were treated respectively in the solutions with different concentrations of substrate at 36° C. for 20 min, and then the cells were resuspended in KPB and washed twice. 10 μL of samples were taken to determine the residual enzyme activity.

Figure 3:
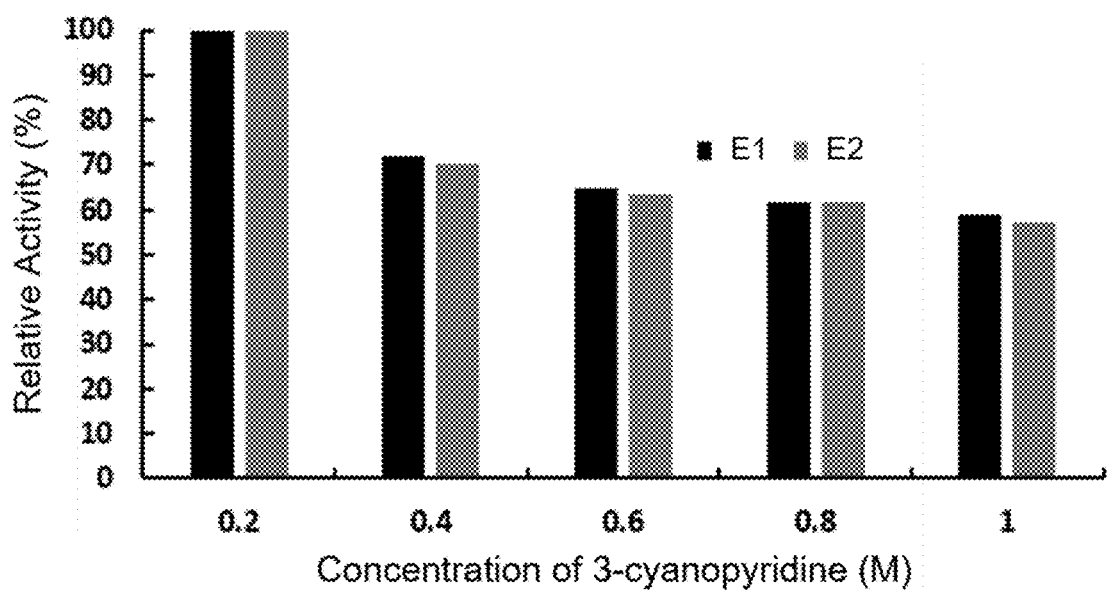
FIG. 3 shows changes in relative enzyme activity at different concentrations of 3-cyanopyridine, wherein bacterium 1: BL21/pET24a-αL6T/A19V/F126Y-βM46K/E108R/S212Y; and bacterium 2: BL21/pET24a-αL6T/A19V/F126Y-βM46K/E108R/S212Y.

As shown in FIG. 3, when the concentration of the substrate 3-cyanopyridine is 0.2 M, the enzyme activity is defined as 100%, and the tolerance to the substrate is not significantly affected after mutation.

Example 5 Determination of Tolerance to Product

Solutions of the product nicotinamide with different concentrations of 0.5 M, 1 M, 1.5 M, and 2 M were prepared. The control and mutant broths with an OD$_{600}$ of 10 at a wavelength of 600 nm were treated respectively in the solutions with different concentrations of product at 36° C. for 20 min, and then the cells were resuspended in KPB and washed twice. 10 μL of samples were taken to determine the residual enzyme activity.

Figure 4:
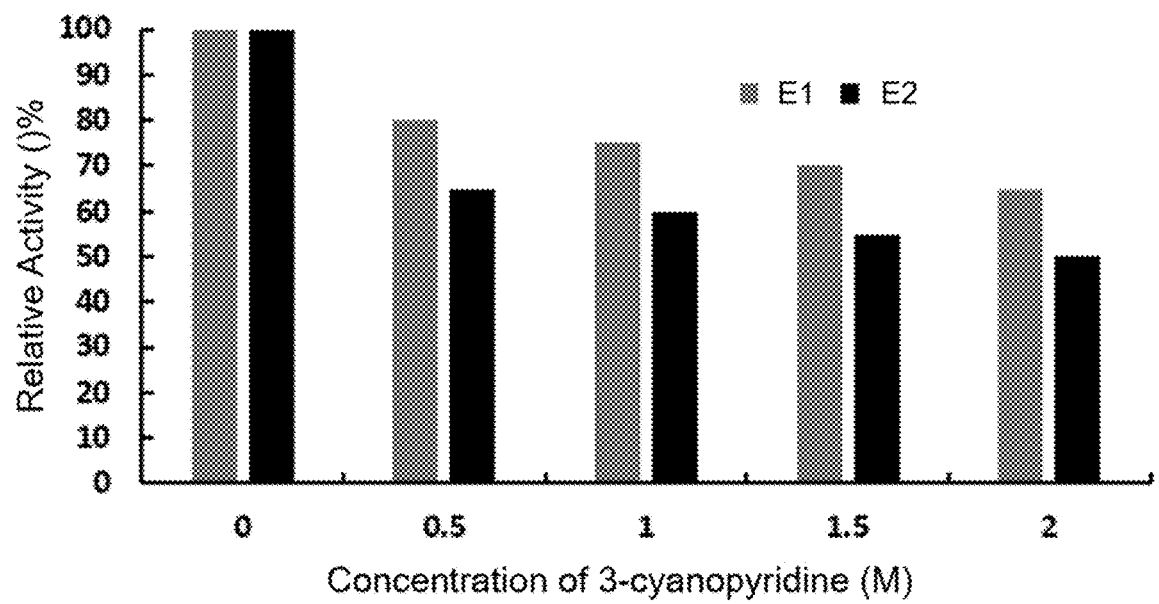
FIG. 4 shows changes in relative enzyme activity at different concentrations of the product nicotinamide, bacterium 1: BL21/pET24a-αL6T/A19V/F126Y-βM46K/E108R/S212Y; and bacterium 2: BL21/pET24a-αL6T/A19V/F126Y-βM46K/G47N/E108R/S212Y.

As shown in FIG. 4, the enzyme activity without treatment with the product was defined as 100%, and it was found that after the mutant was treated with the product nicotinamide of 2 M for 20 min, the residual enzyme activity of the mutant enzyme increased from 28% of the control to 52%. The tolerance of the mutant to the product nicotinamide was significantly improved.

Example 6 High-Density Fermentation of Recombinant *E. coli*

5 mL of LB culture medium containing kanamycin with a concentration of 100 μg/mL was inoculated with the recombinant *E. coli* BL21/pET24a-αL6T/A19V/F126Y-βM46K/G47N/E108R/S212Y, and culture was performed overnight with shaking at 37° C. and 200 r/min. An LB culture medium containing kanamycin with a concentration of 100 μg/mL was inoculated with the above overnight culture at an inoculum concentration of 1%, and culture was performed with shaking at 37° C. and 200 r/min for 6-8 h. A 2 L fermenter fermentation culture medium containing kanamycin with a concentration of 100 μg/mL was inoculated with the above culture at an inoculum concentration of 6%, and feeding culture was performed at 37° C. When the OD$_{600}$ reached 60, the temperature was reduced to 30° C., and 140-150 mL of an inducer was added at a constant flow rate of 0.20-0.22 g/(L·h) to induce the culture for 36 h to end the fermentation. After the fermentation, the enzyme activity reached 24763.48 U/mL.

Example 7 Production of Nicotinamide by Whole-Cell Catalysis

Figure 5:
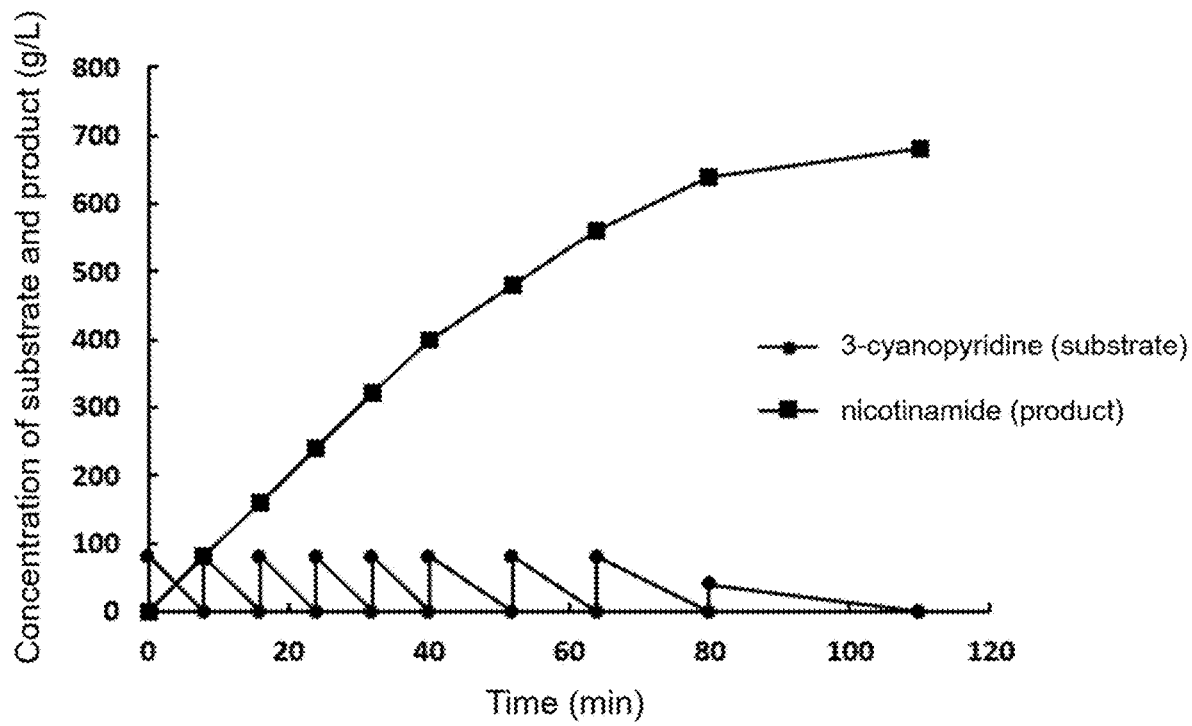
FIG. 5 is a schematic diagram of whole-cell catalytic production of nicotinamide.

The broth after high-density fermentation was centrifuged and collected, washed with water, and centrifuged and collected again. The temperature was adjusted to 25-28° C. 3-cyanopyridine was added to the fermentation broth with an OD$_{600}$ of 150-160.0 at a final concentration of 0.4 mol/L, and stirred continuously. When the present batch of substrate reacted completely, the next batch of substrate was added. The content of each component in the reaction solution was detected by HPLC, and the concentration of nicotinamide was calculated to be 680 g/L, as shown in FIG. 5.

Example 8 Production of Acrylamide by Whole-Cell Catalysis

The broth after high-density fermentation was centrifuged and collected, washed with water, and centrifuged and collected again. The temperature was adjusted to 25-28° C. Acrylonitrile was added to the fermentation broth with an $OD_{600}$ of 150-160.0 at a final concentration of 64 g/L, and stirred continuously. When the present batch of substrate reacted completely, the next batch of substrate was added.

Figure 6:
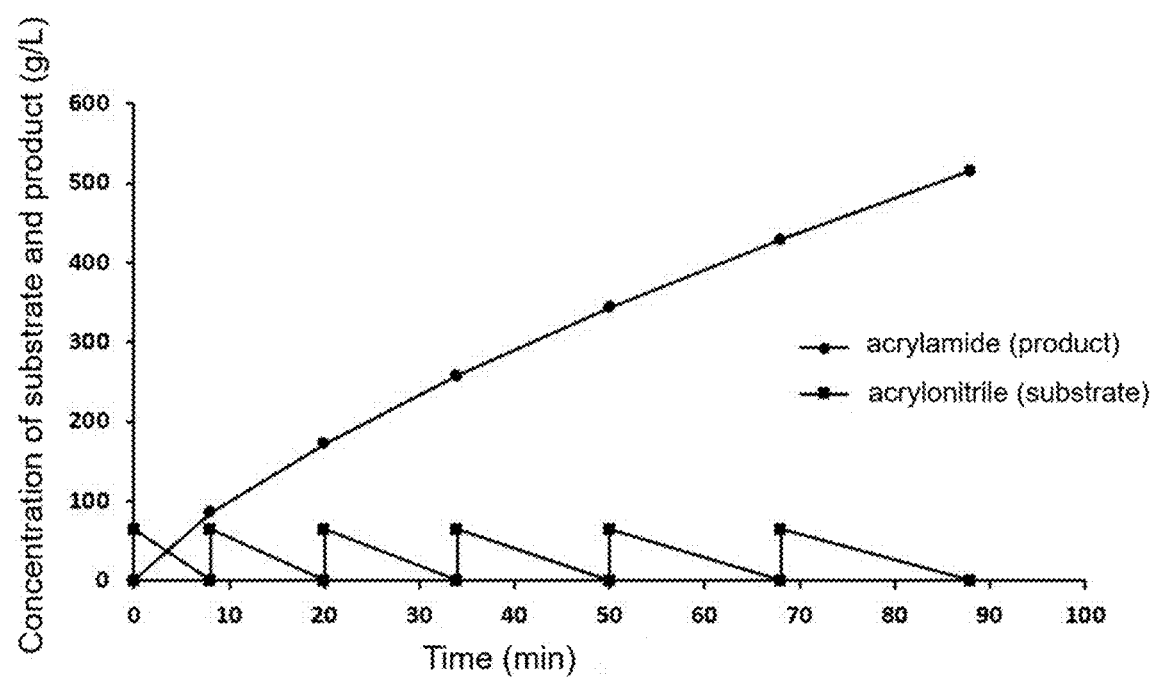
FIG. 6 is a schematic diagram of whole-cell catalytic production of acrylamide.

The content of each component in the reaction solution was detected by HPLC, and the concentration of acrylamide was calculated to be 514.8 g/L, as shown in FIG. 6.

Although the disclosure has been disclosed as above in preferred examples, it is not intended to limit the disclosure. Anyone familiar with this technology can make various changes and modifications without departing from the spirit and scope of the disclosure. Therefore, the protection scope of the disclosure should be defined by the claims.

---

What is claimed is:

1. A nitrile hydratase (NHase) mutant, comprising *Pseudonocardia thermophila* nitrile hydratase (PtNHase) subunits of a PtNHase-α subunit, a PtNHase-β subunit and a regulatory protein PtNHase-p, wherein the amino acid sequence of the PtNHase-α subunit is set forth in SEQ ID NO:1, the amino acid sequence of the PtNHase-β subunit is set forth in SEQ ID NO:2, and the amino acid sequence of the regulatory protein PtNHase-p is set forth in SEQ ID NO:3.

2. A gene encoding the nitrile hydratase mutant of claim 1.

3. The gene of claim 2, wherein the nucleotide sequence is set forth in SEQ ID NO:8.

4. A cell expressing the nitrile hydratase mutant of claim 1.

5. The cell of claim 4, comprising an *Escherichia coli* (*E. coli*) BL21 cell.

6. The cell of claim 5, wherein pET24a(+) is used as an expression vector.

7. The cell of claim 4, wherein a method for constructing the cell is as follows: a gene encoding the nitrile hydratase mutant of claim 1 is ligated with an expression vector, and transformed into *Escherichia coli* (*E. coli*).

8. The cell of claim 7, wherein the gene encoding the nitrile hydratase mutant is set forth in SEQ ID NO:8.

9. The cell of claim 6, wherein the gene encoding the nitrile hydratase mutant as set forth in SEQ ID NO:8 is formed by sequentially ligating the gene encoding the PtN-Hase-β subunit as set forth in SEQ ID NO:2, a gene encoding a spacer sequence a as set forth in SEQ ID NO:6, a gene encoding the PtNHase-α subunit as set forth in SEQ ID NO:1, a gene encoding a spacer sequence b as set forth in SEQ ID NO:7, and a gene encoding the regulatory protein PtNHase-p as set forth in SEQ ID NO:3.

10. A method of using the nitrile hydratase mutant of claim 1, comprising using the nitrile hydratase mutant as a catalyst, and using 3-cyanopyridine or acrylonitrile as a substrate to carry out a transformation reaction for producing nicotinamide or acrylamide.

11. The method of claim 10, wherein with the 3-cyanopyridine or acrylonitrile as the substrate, a cell is used for fermentation, and a fermentation broth is used for whole-cell transformation to produce nicotinamide or acrylamide.

12. The method of claim 11, wherein conditions for the fermentation are as follows: a fermenter culture medium is inoculated with a recombinant *Escherichia coli* (*E. coli*) broth cultured for 6-8 h at an inoculum concentration of 5-8%, and culture is performed at 35-38° C.; when $OD_{600}$ reaches 70-75, a temperature is reduced to 28-30° C., and an inducer is added at a constant flow rate of 0.20-0.22 g/(L·h) to induce the culture for 35-40 h to end the fermentation, wherein the $OD_{600}$ is optical density measured at a wavelength of 600 nm.

13. The method of claim 12, wherein conditions for the whole-cell transformation are as follows: the temperature is adjusted to 25-28° C., a mass ratio of the substrate 3-cyanopyridine to wet bacterial cells is 0.5-2, and a next batch of substrates is added after the substrate reacts completely.

14. The method of claim 12, wherein conditions for the whole-cell transformation are as follows: the temperature is adjusted to 25-28° C., a mass ratio of the substrate acrylonitrile to wet bacterial cells is 1-1.5, and a next batch of substrates is added after the substrate reacts completely.

* * * * *